United States Patent
Mitchell et al.

(10) Patent No.: US 7,057,072 B2
(45) Date of Patent: Jun. 6, 2006

(54) SYNTHESIS AND PURIFICATION OF 1,3,5-TRIAMINO-2,4,6-TRINITROBENZENE (TATB)

(75) Inventors: Alexander R. Mitchell, Livermore, CA (US); Michael D. Coburn, Santa Fe, NM (US); Gregory S. Lee, San Ramon, CA (US); Robert D. Schmidt, Livermore, CA (US); Philip F. Pagoria, Livermore, CA (US); Peter C. Hsu, Pleasanton, CA (US)

(73) Assignee: The Regents of the University of California, Oakland, CA (US)

( * ) Notice: Subject to any disclaimer, the term of this patent is extended or adjusted under 35 U.S.C. 154(b) by 102 days.

(21) Appl. No.: 10/910,659

(22) Filed: Aug. 2, 2004

(65) Prior Publication Data
US 2005/0038297 A1 Feb. 17, 2005

Related U.S. Application Data

(60) Provisional application No. 60/492,037, filed on Aug. 1, 2003.

(51) Int. Cl.
*C07C 209/18* (2006.01)
*C07C 211/50* (2006.01)
*C07C 209/84* (2006.01)

(52) U.S. Cl. .................. 564/403; 564/441; 564/437
(58) Field of Classification Search ................ None
See application file for complete search history.

(56) References Cited

U.S. PATENT DOCUMENTS

| 4,032,377 | A | 6/1977 | Benziger |
| 5,569,783 | A | 10/1996 | Mitchell et al. |
| 5,633,406 | A | 5/1997 | Mitchell et al. |
| 6,069,277 | A | 5/2000 | Mitchell et al. |

OTHER PUBLICATIONS

Energetic Materials Analysis, Diagnostics and Testing, Schmidt et al., 31$^{st}$ International Annual Conference of ICT (2000), Karlsruhe, FRG, p. 37-1 to 37-10.*
Energetic Materials Technology, Manufacturing and Processing, Mitchell et al., 27th International Annual Conference of ICT (1996), Karlsruhe, FRG, p. 29-1 to 29-11.*
Database CAPLUS on STN, Acc. No. 1983:163360, Locke et al., Report (1982), MHSMP-82-31; Order No. DE82022475, 6 pp. Avail.: NTIS From: Energy Res. Abstr. 1982, 7(24), Abstr. No. 63467 (abstract).*
Database CAPLUS on STN, Acc. No. 1991:146412, Firsich et al., Report (1990), MLM-3629; Order No. DE90008176, 14 pp. Avail.: NTIS From: Energy Res. Abstr. 1990, 15(10), Abstr. No. 24330 (abstract).*
Database CAPLUS on STN, Acc. No. 1995:695425, Li et al., Hanneng Cailiao (1993), 1(2), p. 6-11 (abstract).*
A.R. Mitchell et al Advances in the Chemical conversion of Surplus Energetic Materials to Higher Value Products, LLNL Mar. 5, 2001.
E.Y. Spencer et al Preparation of Picramide, Canadian Journal of Research vol. 24 Section B 204-207 (1946).
M.R. Manaa et al Towards Unraveling the Photochemistry of TATB, Thermochimica Acta 384 (2002) 85-90.
G. KH. Khisamutdinov et al A Synthesis of fused benzotriazoles Based on Hexaaminobenzene Derivatives Russian Chemical Bulletin vol. 42, No. 1 Jan. 1993 pp. 136-138.

* cited by examiner

*Primary Examiner*—Brian Davis
(74) *Attorney, Agent, or Firm*—Ann M. Lee; Alan H. Thompson

(57) ABSTRACT

A method to convert surplus nitroarene explosives (picric acid, ammonium picrate,) into TATB is described. The process comprises three major steps: conversion of picric acid/ammonium picrate into picramide; conversion of picramide to TATB through vicarious nucleophilic substitution (VNS) of hydrogen chemistry; and purification of TATB.

10 Claims, 2 Drawing Sheets

US 7,057,072 B2

SYNTHESIS AND PURIFICATION OF 1,3,5-TRIAMINO-2,4,6-TRINITROBENZENE (TATB)

CLAIM OF PRIORITY IN PROVISIONAL APPLICATION

This application is related to Provisional Application No. 60/492,037 filed Aug. 1, 2003 entitled "Synthesis and Purification of 1,3,5-Trianimo-2,4,6-Trinitrobenzene (TATB)", and claims priority thereto under 35 USC 120. Provisional Application No. 60/492,037 is herein incorporated by reference in its entirety.

The United States Government has rights in this invention pursuant to Contract No. W-7405-ENG-48 between the United States Department of Energy and the University of California for the operation of Lawrence Livermore National Laboratory.

BACKGROUND OF THE INVENTION

The global demilitarization of munitions is producing millions of pounds of surplus explosives. Historically, surplus explosives have been disposed of by open burning/open detonation (OB/OD). The disposal of these materials by OB/OD is becoming unacceptable due to public concerns and increasingly stringent environmental regulations.

Triaminotrinitrobenzene (TATB) is a reasonably powerful high explosive that's thermal and shock stability is considerably greater than that of any other known material of comparable energy (S. F. Rice et al., "The Unusual Stability of TATB: A Review of the Scientific Literature", Lawrence Livermore National Laboratory, Livermore, Calif., UCRL-LR-103683, July 1990). It is used in military applications because of its significant insensitivity to thermal and shock environments (B. M. Dobratz, "The Insensitive High Explosive Triaminotrinitrobenzene (TATB): Development and Characterization—1888 to 1994," Los Alamos Scientific Laboratory, Los Alamos, N. Mex., Report LA-13014-H, August, 1995). In the civilian sector, perforating guns containing TATB have been designed for deep oil well explorations where heat-insensitive explosives are required. (W. E. Voreck, et al, "Shaped Charge for a Perforating Gun Having a Main Body of Explosive Including TATB and a Sensitive Primer", U.S. Pat. No. 5,597,974). TATB is also used to produce benzenehexamine, an intermediate in the synthesis of new, advanced materials. (See D. Z. Rogers, "Improved Synthesis of 1,4,5,8,9,12-Hexaazatriphenylene," J. Org. Chem., 51, 3904 (1986) and R. Breslow, et al, "Synthesis of the Hexaaminobenzene Derivative Hexaazaoctadecahydrocoronene (HOC) and Related Cations, J.Am. Chem. Soc., 106, 6453 (1984). In addition, the use of TATB to prepare components of liquid crystals for use in display devices has been described (K. Praefcke and B. Kohne, "Amido Compounds as Components of Lyotropic Liquid-Crystal Phases, Ger. Offen. DE 3,612,238 (1988); Chemical Abstracts, 108, 159109n.)

The conversion of picric acid or ammonium picrate into picramide often involves the use of noxious, toxic chemicals ($SOCl_2$, $POCl_3$, $NH_3$). The direct conversion of picric acid to picramide is disclosed by E. Y. Spencer and G. F. Wright in, "Preparation of Picramide," Canadian Journal of Research, 24B, 204 (1946). This procedure describes the reaction of molten picric acid (173° C.) and urea to produce picramide in the form of an intractable glass. The major drawbacks to this procedure are: (1) molten picric acid, especially at such an elevated temperature (173° C.), is a recognized hazard; (2) the picramide is produced as a solid glass product that cannot be safely and efficiently removed from an industrial scale reactor; and (3) cyanuric acid is produced as a co-product with picramide and must be removed by extraction.

BRIEF DESCRIPTION OF THE DRAWINGS

The accompanying drawings, which are incorporated into and form part of this disclosure, illustrate embodiments of the invention and together with the description, serve to explain the principles of the invention.

SUMMARY OF THE INVENTION

An aspect of the invention includes a method comprising: suspending picric acid or ammonium picrate with an ammonium salt in a dipolar aprotic solvent; heating the suspension from 2 to 22 hours to a temperature in the range of 175 to 185° C. under a pressure ranging from 20 to 80 psi to form picramide; converting the picramide via VNS chemistry to crude TATB; acetylating the crude TATB to form triacetyl-TATB; treating the triacetyl-TATB with activated carbon; and ammonolyzing the carbon-treated triacetyl-TATB to form purified TATB.

DETAILED DESCRIPTION

Figure 1:
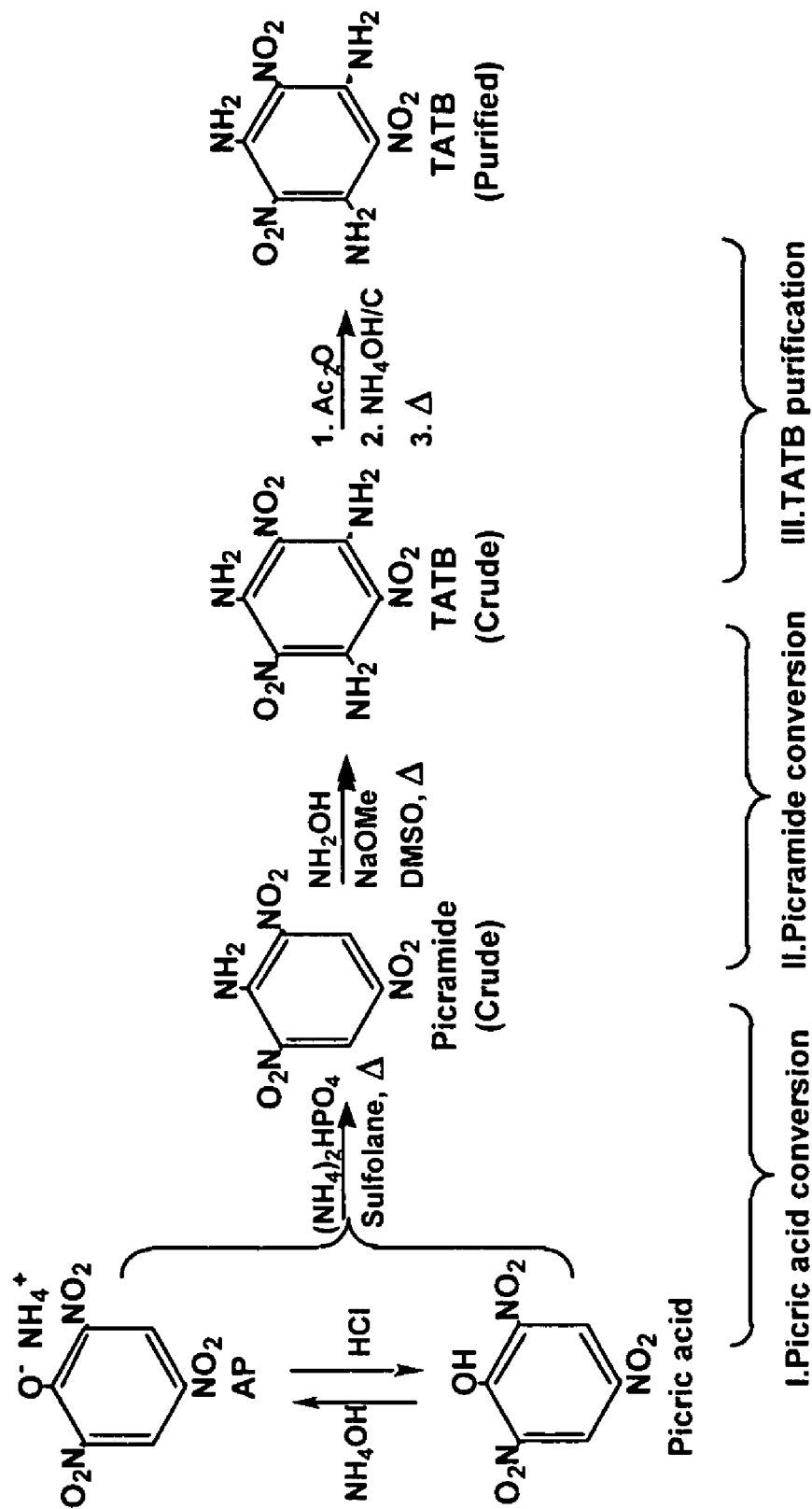
FIG. 1 shows the 3-step conversion of picric acid or ammonium picrate to TATB.

A method to convert surplus nitroarene explosives (picric acid, ammonium picrate,) into TATB is disclosed herein. The process comprises three major steps: conversion of picric acid/ammonium picrate into picramide; conversion of picramide to TATB through vicarious nucleophilic substitution (VNS) of hydrogen chemistry; and purification of TATB. The synthetic route is shown in FIG. 1. Picramide is formed by suspending picric acid or ammonium picrate with an ammonium salt in a dipolar aprotic solvent and then heating the suspension under low pressure. The mole equivalents of ammonium salt to picric acid ranges from 2 to 30 and the mole equivalents of ammonium salt to ammonium picrate ranges from 1 to 30. The suspension is typically heated between 2 to 22 hours to a temperature in the range of 175 to 185° C. under 20 to 80 psi of pressure.

Conversion of Picric Acid/Ammonium Picrate to Picramide

Treatment of molten picric acid with urea (173° C., 36 hours) produces a mixture of picramide, urea and cyanuric acid. Removal of urea and cyanuric acid by extractions with the appropriate solvents (e.g., water and acetone) affords picramide in 88% yield (E. Y. Spencer and G. F. Wright, Can. J. Research, 24B, 204, 1946). Molten picric acid, especially at such an elevated temperature (173° C.), is a recognized hazard. The picramide produced by this process results in a solid glass product, which cannot be safely and efficiently removed from an industrial scale reactor. Conversion of picric acid/ammonium picrate to picramide using a solvent (e.g., sulfolane) improves upon the process described in Spencer et al. by allowing the safe conversion of picric acid and ammonium picrate (Explosive D) to picramide and cyanuric acid. High concentrations of reactants are used as described in Example 1 below.

Replacement of urea with an ammonium salt (or "$NH_3$ reagent") obtained from ammonia and weak acids (e.g., acetic, carbonic acid, phosphoric acid) produces picramide free of cyanuric acid. Thus, reaction of picric acid or ammonium picrate with an ammonium salt in dipolar aprotic solvents such as sulfolane or N-methylpyrrolidinone (NMP) for several hours at 175–185° C., followed by a water wash, produces picramide that is free of cyanuric acid and ammonium salts. Ammonium hydroxide (28% $NH_3$ in $H_2O$) is unsatisfactory for use as an $NH_3$ reagent as picric acid/ammonium picrate are decomposed to black solids when exposed to the ammonium hydroxide. Example 2 and Table 1 list conversions of 0.18–0.92 g of ammonium picrate in sulfolane to picramide in 8 ml glass pressure tubes.

TABLE 1

Conversion of Ammonium Picrate to Picramide[a]

| Entry | Time (h) | T (° C.)[b] | Ammonium Picrate eq | mol/L | Ammonium Salt eq | mol/L | Picramide % Yield |
|---|---|---|---|---|---|---|---|
| 1 | 2<br>5 | Rt→177<br>177 | 1 | 0.25 | $(NH_4)_2HPO_4$<br>10 | 2.5 | 76 |
| 2 | 2<br>6 | Rt→177<br>177 | 1 | 1.25 | $(NH_4)_2HPO_4$<br>2.0 | 2.5 | 87 |
| 3 | 2<br>6 | Rt→177<br>177 | 1 | 0.25 | $NH_4CO_2NH_2$<br>10 | 2.5 | 68 |
| 4 | 2<br>6 | Rt→177<br>177 | 1 | 1.25 | $NH_4CO_2NH_2$<br>2.0 | 2.5 | 87 |
| 5 | 2 | 177 | 1 | 0.25 | $NH_4CO_2NH_2$<br>10 | 2.5 | 28 |
| 6 | 2 | 177 | 1 | 0.25 | $NH_4HCO_3$<br>10 | 2.5 | 16 |
| 7 | 2 | 177 | 1 | 0.25 | $NH_4OAc$<br>20 | 5.0 | 32 |

[a]All reactions were performed in 8 mL Teflon ® capped glass pressure tubes containing 3 mL sulfolane and 0.18–0.92 g of ammonium picrate.
[b]rt = room temperature.

Example 3 and Table 2 list conversions of 0.92 to 10.8 g substrate (ammonium picrate or picric acid) to picramide when the reaction is run in a 450 ml stainless steel reactor for longer periods of time. The pressure in the reactor does not exceed 40 psi. The highest conversions of ammonium picrate or picric acid to picramide (87–94%) are obtained when the ammonium salt is diammonium hydrogen phosphate [$(NH_4)_2HPO_4$] or ammonium carbamate ($NH_4CO_2NH_2$) and the substrate concentrations are between 1.1–2.5 M. The use of picric acid as a substrate requires twice the mole equivalents of ammonium salt as needed for the conversion of ammonium picrate to picramide (Table 2, entries 4 and 5). The picramide obtained in these syntheses is used, without purification, to produce TATB.

TABLE 2

Conversion of Ammonium Picrate or Picric Acid to Picramide[a]

| Entry (solvent) | Time (h) | T (° C.)[b] | Substrate eq | mol/L | Ammonium Salt eq | Mol/L | % Yield |
|---|---|---|---|---|---|---|---|
| 1 (sulfolane) | 2<br>20 | rt→175<br>175 | Ammonium Picrate<br>1 | 0.09 | $(NH_4)_2HPO_4$<br>2.0 | 0.19 | 30 |
| 2 (NMP) | 2<br>20 | rt→175<br>175 | Ammonium Picrate<br>1 | 0.09 | $NH_4CO_2NH_2$<br>28 | 2.5 | 56 |
| 3 (sulfolane) | 2<br>20 | rt→175<br>175 | Ammonium Picrate<br>1 | 0.25 | $(NH_4)_2HPO_4$<br>10 | 2.5 | 88 |
| 4 (sulfolane) | 2<br>20 | rt→175<br>175 | Ammonium Picrate<br>1 | 1.1 | $(NH_4)_2HPO_4$<br>1.0 | 1.1 | 94 |
| 5 (sulfolane) | 2<br>20 | rt→175<br>175 | Picric Acid<br>1 | 1.1 | $(NH_4)_2HPO_4$<br>2.0 | 2.2 | 93 |

[a]All reactions were performed in a sealed 450 mL Parr ® stainless steel reactor containing 40 mL solvent (sulfolane or NMP) and 0.92–10.8 g of ammonium picrate or picric acid.
[b]rt = room temperature.

Example 1

A slurry of picric acid (2.29 g, 0.01 mol) and urea (1.80 g, 0.03 mol) in sulfolane (2 mL) is heated (167° C.) in a closed pressure vessel for 23 h. $^{13}$C-NMR analysis indicates quantitative conversion to picramide and cyanuric acid. Under the same conditions, ammonium picrate (2.46 g, 0.01 mol) and urea (1.80 g, 0.03 mol) in sulfolane (2 mL) gave a complete conversion to picramide and cyanuric acid.

Example 2

(a) Ammonium picrate (0.18 g, 0.75 mmol) and diammonium hydrogen phosphate (0.99 g, 7.5 mmol) are suspended in dry sulfolane (3 ml) and stirred in a Teflon® capped glass pressure tube (8 ml) for 2 hr with the application of heat, which raises the temperature of the reaction from 25° C. to 177° C. The reaction is continued an additional 5 hr at 177° C. and cooled to ambient temperature. Water (30 ml) is added to the slurry and the product is collected and washed with water. Vacuum drying yields 0.13 g (76%) of picramide (Table 1, entry 1).

(b) Ammonium picrate (0.92 g, 3.7 mmol) and diammonium hydrogen phosphate (0.99 g, 7.5 mmol) are suspended in dry sulfolane (3 ml) and stirred in a Teflon® capped glass pressure tube (8 ml) for 2 hr with the application of heat, which raises the temperature of the reaction from 25° C. to 177° C. The reaction is continued an additional 5 hr at 177° C. and cooled to ambient temperature. Water (30 ml) is added to the slurry and the product is collected and washed with water. Vacuum drying yields 0.74 g picramide (87%) (Table 1, entry 2).

(c) Ammonium picrate (0.18 g, 0.75 mmol) and ammonium carbamate (0.59 g, 7.5 mmol) are suspended in sulfolane (3 ml) and stirred for 2 hr with the application of heat which raises the temperature of the reaction from 25° C. to 177° C. The reaction is continued an additional 6 hr at 177° C. and cooled to ambient temperature. Water (30 ml) is added to the slurry and the product is collected, washed with water and dried to yield 0.12 g (68%) of picramide (Table 1, entry 3).

(d) Ammonium picrate (0.92 g, 3.7 mmol) and ammonium carbamate (0.59 g, 7.5 mmol) are suspended in sulfolane (3 ml) and stirred for 2 hr with the temperature of the reaction increasing from 25° C. to 177° C. The reaction is continued an additional 6 hr at 177° C. and cooled to ambient temperature. Water (30 ml) is added to the slurry and the product is collected, washed with water and dried to yield 0.75 g (87%) of picramide (Table 1, entry 4).

(e) Ammonium picrate (0.18 g, 0.75 mmol) and ammonium carbamate (0.59 g, 7.5 mmol) are suspended in sulfolane (3 ml) and stirred for 2 hr with the application of heat which raises the temperature of the reaction from 25° C. to 177° C. The reaction is continued an additional 2 hr at 177° C. and cooled to ambient temperature. Water (30 ml) is added to the slurry and the product is collected, washed with water and dried to yield 0.12 g (68%) of picramide (Table 1, entry 5)

(f) Ammonium picrate (0.18 g, 0.75 mmol) and ammonium bicarbonate (0.59 g, 7.5 mmol) are suspended in sulfolane (3 ml), stirred for 2 hr at 177° C., cooled to ambient temperature and mixed with water (30 ml). The product is collected, washed with water and dried to yield 0.030 g (16%) of picramide (Table 1, entry 6).

(g) Ammonium acetate (1.16 g, 15.0 mmol) and ammonium picrate (0.18 g, 0.75 mmol) are suspended in sulfolane (3 ml), stirred for 2 hr at 177° C., cooled to ambient temperature and mixed with water (30 ml). The product is collected, washed with water and dried to yield 0.061 g (32%) of picramide (Table 1, entry 7).

Example 3

(a) Ammonium picrate (0.92 g, 3.7 mmol), diammonium hydrogen phosphate (0.99 g, 7.5 mmol) and dry sulfolane (40 ml) are placed in a glass-lined, stainless steel reactor. The reactor is sealed and the reaction slurry is stirred with heating for 2 hr as the temperature increases from 25 to 175° C. (20 psi pressure). The temperature is maintained at 175° C. and stirring is continued for an additional 20 hr. The cooled reaction mixture is mixed with water (400 ml) and the insoluble material is collected, washed with water and dried to give 0.26 g (30%) picramide (Table 2, entry 1).

(b) Ammonium picrate (0.92 g, 3.7 mmol), ammonium carbamate (7.78 g, 99.6 mmol) and dry N-methylpyrrolidinone (40 ml) are placed in a glass-lined, stainless steel reactor. The reactor is sealed and the reaction slurry is stirred with heating for 2 hr as the temperature increases from 25 to 175° C. (80 psi pressure). The temperature is maintained at 175° C. and stirring is continued for an additional 20 hr. The cooled reaction mixture is mixed with water (400 ml) and the insoluble material is collected, washed with water and dried to give 0.52 g (56%) picramide (Table 2, entry 2).

(c) Ammonium picrate (2.45 g, 9.95 mmol), diammonium hydrogen phosphate (13.2 g, 100 mmol) and dry sulfolane (40 ml) are placed in a glass-lined, stainless steel reactor to form a 0.25 M concentration reaction slurry. The reactor is sealed and the reaction slurry is stirred with heating for 2 hr as the temperature increases from 25 to 175° C. (40 psi pressure). The temperature is maintained at 175° C. and stirring is continued for an additional 20 hr. The cooled reaction mixture is mixed with water (400 ml) and the insoluble material is collected, washed with water and dried to give 1.99 g picramide obtained in 88% yield (Table 2, entry 3).

(d) Ammonium picrate (10.8 g, 43.8 mmol), diammonium hydrogen phosphate (5.79 g, 43.8 mmol) and dry sulfolane (40 ml) are placed in a glass-lined, stainless steel reactor to form a 1.1M concentration reaction slurry. The reactor is sealed and the reaction slurry is stirred with heating for 2 hr as the temperature increases from 25 to 175° C. (20 psi pressure). The temperature is maintained at 175° C. and stirring is continued for an additional 20 hr. The cooled reaction mixture is mixed with water (400 ml) and the insoluble material is collected, washed with water and dried to give picramide obtained in 94% yield (Table 2, entry 4).

(e) Picric acid (10.0 g, 43.8 mmol), diammonium hydrogen phosphate (11.6 g, 87.6 mmol) and dry sulfolane (40 ml) are placed in a glass-lined, stainless steel reactor to form a 1.1M concentration reaction slurry. The reactor is sealed and the reaction slurry is stirred with heating for 2 hr as the temperature increases from 25 to 175° C. (20 psi pressure). The temperature is maintained at 175° C. and stirring is continued for an additional 20 hr. The cooled reaction mixture is mixed with water (400 ml) and the insoluble material is collected, washed with water and dried to produce picramide in 93% yield (Table 2, entry 5).

Conversion of Picramide to TATB Using VNS

The conversion of picramide to TATB using VNS chemistry is disclosed in U.S. Pat. Nos. 5,569,783 and 5,633,406 and 6,069,277, assigned to the same assignee and incorporated herein by reference. Optimizations of VNS reagents, solvents, temperature and other parameters related to the VNS production of TATB are disclosed herein. General aspects of VNS chemistry are reviewed by Makosza, et al, in "Vicarious Nucleophilic Substitution of Hydrogen," Accounts of Chemical Research, 20, 282 (1987) and "Nucleophilic Substitution of Hydrogen in Heterocyclic Chemistry", Chemical Reviews, 104, 2631 (2004). See also Chupakhin, et al, "Nucleophilic Aromatic Substitution of Hydrogen"; Academic Press: San Diego, Calif., 1994 and A. R. Katritzky, et al, "Direct Amination of Nitrobenzenes by Vicarious Nucleophilic Substitution", J.Org.Chem., 51, 5039 (1986). Reaction conditions, depending on the particular VNS reagent employed, that allow the partial or full replacement of DMSO with less expensive solvents are disclosed herein. U.S. Pat. No. 5,569,783, discloses DMSO as the most effective solvent in the VNS synthesis of TATB, while the use of MEOH as the solvent, even at elevated temperatures, yielded DATB as the major product.

In an effort to improve the synthesis reported in the prior art by reducing the amount of DMSO, the use of diluents such as MeOH and toluene for the VNS synthesis was investigated. Disclosed herein are the surprising effect that these diluents had on the yields and purity of the TATB product. Good to excellent yields of TATB from picramide using MeOH, mixtures of toluene and MeOH, and mixtures of toluene, MeOH, and DMSO are disclosed herein. The synthesis involves reacting a VNS reagent with picramide in the selected solvent/solvent mixture and heating to reflux temperatures while concomitantly distilling off the solvent. For example, when ATA reacts with picramide in MeOH or a mixture of toluene and MeOH at 60° C. and the solvent is removed under vacuum, TATB is obtained in high yields.

It has been previously shown that Hydroxylamine, the least expensive VNS reagent, in combination with a strong base, an aprotic dipolar solvent (e.g., DMSO) and an elevated temperature (65–95° C.), reacts with picramide to yield TATB in 50–74% yield with about 97% purity. The concentration of picramide is typically 0.1 to 0.25 M which gives rise to highly viscous reaction suspensions. When picramide concentration is higher than 0.25 M, the reaction suspensions cannot be efficiently stirred. In addition, lower yields of TATB along with elevated levels of the partially aminated product, diamino-2,4,6-trinitrobenzene (DATB), and the mono nitroso analog of TATB (TADNB).

DMSO is an effective solvent in the VNS synthesis of TATB. However, DMSO is expensive in relation to other industrial solvents. The substitution of DMSO by methanol or toluene or methanol-toluene mixtures predictably provides TATB in lower yield and contaminated with DATB from the incomplete amination of picramide. Hence, reaction of picramide with 4-amino-1,2,4-triazole (ATA) in methanol (60° C.) in the presence of sodium methoxide provides primarily DATB and little or no TATB (See U.S. Pat. No. 5,569,783). Unexpectedly, when the reaction is conducted in methanol and methanol is removed under vacuum (~0.25 atm) to take the reaction mixture to dryness, an almost quantitative yield of TATB is obtained using ATA as VNS reagent (Example 4). Alternatively, when the reaction is run in methanol and toluene, taken to dryness and resuspended in toluene, TATB is obtained in high yield (98%) (Example 5).

Although hydroxylamine is the least reactive VNS reagent studied, it is inexpensive and available in bulk quantities while the VNS reagents ATA and trimethylhydrazinium iodide (TMHI) are significantly more costly and not available in bulk quantities. The use of diluents such as MeOH and toluene allow the VNS synthesis using hydroxylamine to be run in more dilute solutions, allowing better stirring, while keeping the volume of DMSO at a minimum. The VNS synthesis is not as efficient using hydroxylamine as the aminating reagent. Use of some DMSO ensures that the synthesis goes to competion and only TATB is obtained. Mixtures of toluene and MeOH with DMSO yield TATB in 92% when reacted at 60° C. The synthesis involves heating the mixture at 60° C. under vacuum (about 0.25 atm), thus removing the volatile MeOH and toluene, and further heating the concentrated DMSO solution at 90° C. for 1.5 hr. The addition of MeOH and toluene allow the synthesis to initially be run in a more dilute solution. This process is an improvement over the previous method in both the purity and yield of the product, TATB. (See Example 6).

In another embodiment, heat (without vacuum) is supplied to a reaction of a hydroxlamine salt (e.g., hydrochloride, sulfate, phosphate) and, as the reaction temperature increases from ambient to 90° C., methanol (bp. 64.7° C.) and toluene (bp.110.6° C.) distill off from the reaction suspension as a methanol (72.5%)-toluene (27.5%) azeotrope (bp. 63.5° C.). The addition of miscible, low boiling solvents (methanol, toluene) to DMSO at the outset of the reaction significantly reduces viscosity which in turn allows efficient stirring and scalability of the reaction. The loss of methanol and toluene with the increase of reaction temperature increases the reactant concentrations (favoring reaction kinetics) without affecting the viscosity and ease of stirring of the reaction suspension. For example, in example 7, hydroxylamine hydrochloride and picramide react in a mixture of methanol, toluene and DMSO containing sodium methoxide. The stirring reaction slurry is heated from ambient temperature to 90° C. over 45 minutes during which time most of the methanol and toluene distill off. The reaction slurry is then stirred an additional 90 min (90° C.), cooled, quenched and worked up to provide TATB in 85% yield.

Prolonged treatment of yellow TATB with hydroxylamine and strong base at elevated temperature can produce a TATB-derived impurity that results in a discolored or "green" TATB. Similarly, exposure of TATB to UV irradiation produces green TATB. As one synthesis of TATB disclosed herein entails the use of hydroxylamine, base and elevated temperature (60–90° C.), the production of discolored ("green") TATB containing small amounts of 1,3,5-triamino-2,4-dinitro-6-nitrosobenzene (TADNB) is expected. When the conversion of picramide to TATB is not 100% efficient, some DATB (1,3-Diamino-2,4,6-trinitrobenzene) is expected.

Example 4

A suspension of picramide (0.274 g, 1.20 mmol), ATA (0.504 g, 6.00 mmol) and sodium methoxide (0.610 g, 11.3 mmol) in methanol (7.4 ml) is stirred with heating (25 to 60° C.) in a 30 ml reaction tube that is held under vacuum for 0.5 hr. The dried mixture is kept under vacuum for 21 hr at 60° C. The reaction tube is cooled (4° C. ) and acetic acid (10 ml) is added. The resulting precipitate is collected, washed with water and dried to yield 0.309 g (99.8%) of a dull yellow solid. The IR spectra for this material and TATB are identical.

Example 5

A suspension of picramide (0.274 g, 1.20 mmol), ATA (0.504 g, 6.00 mmol), sodium methoxide (0.610 g, 11.3 mmol) in methanol (3.8 ml) and toluene (3.6 ml) is stirred with heating (25 to 60° C.) in a 30 ml reaction tube that is held under vacuum for 1.5 hr. The reaction tube is cooled to 25° C., the vacuum is removed and toluene (4.8 ml) is added. The suspension is stirred at 60° C. for 15 hr (calcium sulfate protection), cooled to 4° C. and quenched with acetic acid (10 ml). The resulting precipitate is collected, washed with water and dried to yield 0.283 g (98%) of TATB (a dull yellow solid).

Example 6

A suspension of picramide (0.274 g, 1.20 mmol), 50% aqueous hydroylamine (0.37 ml, 6.00 mmol) and sodium methoxide (0.610 g, 11.3 mmol) in a mixture of methanol (2.6 ml), toluene (2.4 ml) and DMSO (2.4 ml) is stirred with heating (25 to 60° C.) in a 30 ml reaction tube that is held under vacuum for 40 min. The vacuum is removed and the suspension is stirred at 60° C. for 7 hr under a dry atmosphere, cooled to 4° C. and quenched with acetic acid. The resulting precipitate is collected, washed with water and dried to yield 0.285 g (92%) of TATB (a tan solid).

Example 7

A suspension of picramide (1.10 g, 4.81 mmol) and hydroxylamine hydrochloride (1.67 g, 24.0 mmol) is suspended in a mixture of toluene (19.2 ml) and DMSO (14.4 ml). A 25 wt. % solution of sodium methoxide in methanol (16.8 ml, 69.8 mmol) is added and the reaction mixture is stirred with heating (25 to 90° C.) over a 50 min period while most of the methanol and toluene distill from the reaction mixture. The reaction slurry is stirred (90° C.) for 90 min and cooled prior to quenching with a solution containing acetic acid (5.6 ml) and toluene (4.8 ml). The resulting precipitate is collected, washed (30 ml acetone, 60 ml water) and dried to give 1.06 g TATB (85%). FTIR analysis indicates the presence of DATB (0.9%) and TADNB (1.2%).

Purification of TATB

It is desirable to have effective purification procedures in place so that TATB can be recovered from TATB containing unacceptable levels of impurity. The major obstacle to TATB purification is the very low solubility of TATB in most solvents (e.g., 0.047% solution in DMSO at 21° C.). This obstacle is overcome by converting impure TATB preparations to relatively soluble derivatives which, after purification, are converted to purified TATB by ammonolysis. Impure TATB generally contains impurities ranging from 1–15%. Reaction conditions for ammonolysis generally range from 90–130° C. for 0.5–4 hours.

Two procedures have been developed to remove impurities that may form during a VNS synthesis of TATB employing hydroxylamine, strong base and elevated temperature (60–90° C.). Small amounts of 1,3,5-triamino-2,4-dinitro-6-nitrosobenzene (TADNB) as well as DATB (1,3-Diamino-2,4,6-trinitrobenzene) can be expected when the conversion of picramide to TATB is not 100% efficient. In addition, the production of TATB from crude picramide can carry over low level impurities residing in the unpurified picramide.

The first procedure utilizes the finding that the solubility of TATB in DMF or DMSO (0.047% at room temperature) can be increased 20-fold through the formation of a TATB sodium salt. Treatment of the TATB sodium salt prepared from pure TATB with aqueous inorganic acids regenerates pure, fine particle size TATB (U.S. Pat. No. 6,225,503). However, the same treatment of a TATB sodium salt prepared from impure TATB does not yield purified TATB. It has been found that treatment of an impure TATB sodium salt with activated carbon followed by acidification produces purified TATB. This procedure is best employed for TATB preparations containing low-level ($\leq$5%) impurities.

Figure 2:
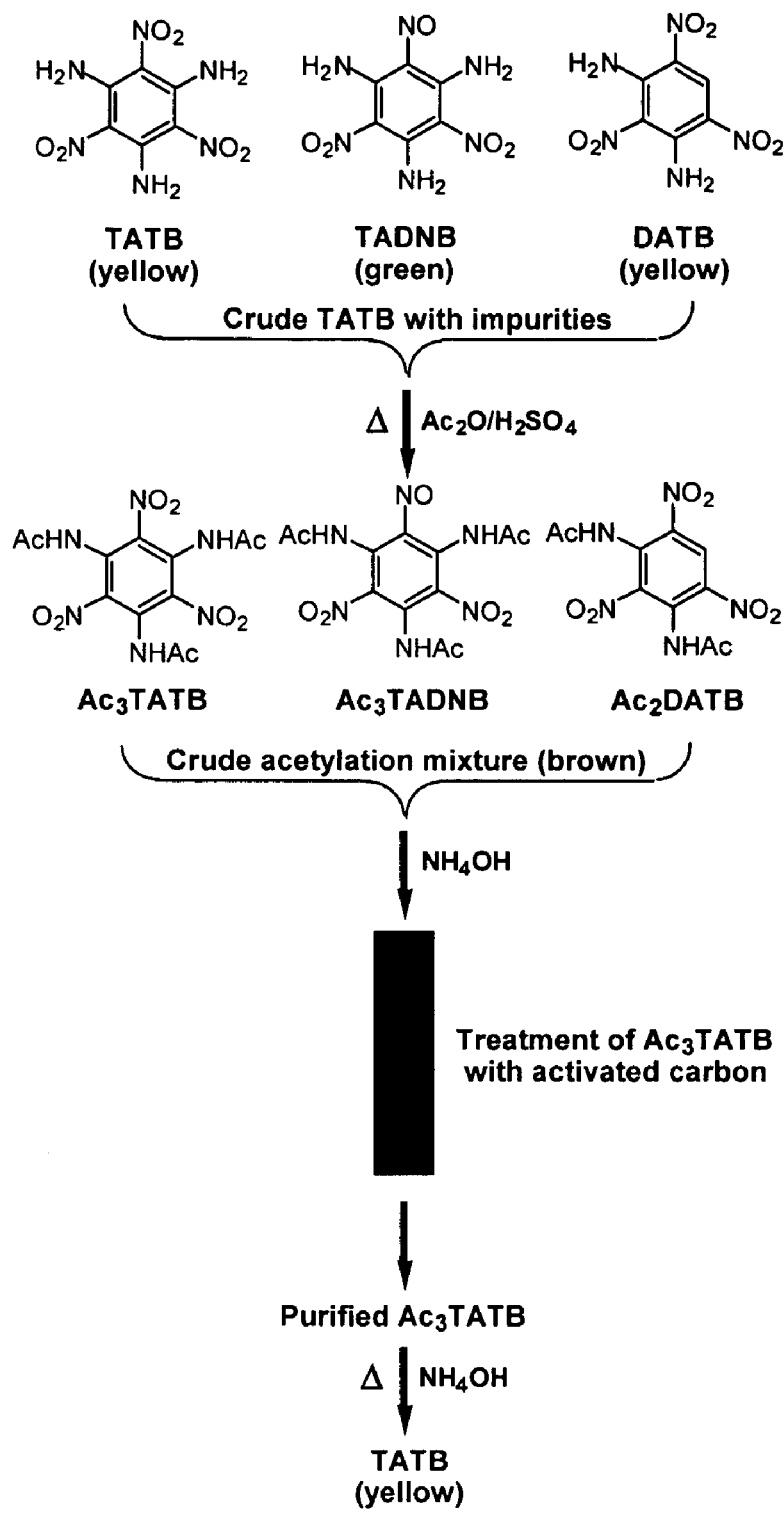
FIG. 2 shows a purification scheme of TATB via a triacetyl-TATB derivative.

The second procedure utilizes an acetylation reaction. Referring to FIG. 2, a pathway to purification of TATB via an acetyl derivative is shown. Acetylation of TATB reported by G. K. Khisamutinov, et al, ("The Synthesis of Fused Benzotriazoles Based on Hexaaminobenzene Derivatives," Russian Chemical Bulletin, 42, 136, 1993) is improved through the use of 10-fold more sulfuric acid catalyst. Crude TATB (containing TADNB, DATB and other impurities) is acetylated to provide crude triacetyl-TATB ($Ac_3$-TATB) which is dissolved in $NH_4OH$ (28% $NH_3$ in $H_2O$) and treated with activated carbon (column or batchwise) to produce a solution of purified $Ac_3$-TATB in $NH_4OH$. The solution is heated (sealed vessel) to effect ammonolysis of the $Ac_3$-TATB and yield purified TATB. $Ac_3$-TATB has good solubility in ammonium hydroxide and solutions containing up to 10% $Ac_3$-TATB have been prepared. TATB, as expected, is very insoluble in ammonium hydroxide. The ammonolysis of Ac3-TATB has been studied in the temperature range from 20–130° C. using $NH_4OH$ (28% $NH_3$ in water) as well as mixtures of $NH_4OH$ and DMF. Ammonolyses ($\leq$2 hr) at temperature $\leq$100° C. produce TATB and unreacted $Ac_3$-TATB (Example 9) while ammonolyses ($\geq$0.5 hr) at $\geq$120° C. yield only TATB. Purified TATB is obtained in 50 to 80% yields depending on the impurity levels in the original TATB.

A sample of impure TATB containing DATB (4%) and TADNB (11%) was acetylated, treated with activated carbon and ammonolyzed. TATB was obtained with no detectable DATB or TADNB (Example 12). In addition, the DSC for the purified TATB gives an exotherm peak @ 382.29° C. compared with an exotherm peak @ 377.26° C. obtained with production grade TATB prepared by the Benziger procedure (U.S. Pat. No. 4,032,377).

Example 8

Acetylation of TATB

TATB (15.0 g, 0.058 mol) is suspended in acetic anhydride (100 ml, 1.06 mol) and sulfuric acid (1.30 ml, 0.024 mol) is added with stirring. The suspension is stirred with heating (20 to 98° C.) for 1 hr and stirred an additional 4 hr. at 98° C. The suspension is cooled to 4° C. and treated with ice water (100 ml). The suspension is heated to 98° C. with stirring (1 hr), cooled to 25° C. and filtered. The collected product is washed with water (400 ml) and dried to give 20.8 g (93%) of light tan solid with an IR spectrum identical to that for known 1,3,5-triacetamido-2,4,6-trinitrobenzene (known as Ac3-TATB or triacetyl-TATB in this invention).

Example 9

Conversion of Acetyl Derivative Back to TATB (First Procedure)

$Ac_3$-TATB (1.26 g, 3.12 mmol) is dissolved in 30 ml DMF and placed in a pressure bottle containing 30 ml ammonium hydroxide (28% $NH_3$ in water) and a magnetic stirring bar. The solution is stirred with heating from ambient temperature to 96° C. (0.5 hr) to produce a deep orange suspension. The suspension is stirred at 96° C. (2 hr), cooled to 4° C., filtered, washed with DMF-water (1:1) and water to provide 0.627 g of a yellow solid (78%) with an IR spectrum identical to that for known TATB. The pooled filtrate and washes yielded lemon yellow crystals (0.241 g) with an IR spectrum identical to that for known $Ac_3$-TATB (19% recovery).

Example 10

Conversion of Acetyl Derivative back to TATB (Second Procedure)

$Ac_3$-TATB (7.70 g, 20.0 mmol) is placed in a glass-lined, stainless steel reactor containing 50 ml DMF and 50 ml ammonium hydroxide (28% $NH_3$ in water). The reactor is sealed and the reaction mixture is stirred for 20 min as the temperature is increased from 25 to 120° C. The temperature is held at 120–130° C. for 40 min (170 psi) and the reactor is cooled to ambient temperature. The resulting suspension is filtered and the collected product is washed with water and dried to yield 3.52 g (68%) of TATB.

Example 11

Conversion of Impure $Ac_3$-TATB Back to TATB without Carbon Filtration

Impure TATB was acetylated and converted back to TATB without first treating the solution with activated carbon. TATB containing 4% DATB and 11% TADNB is reacted with acetic anhydride and $H_2SO_4$ to provide $Ac_3$-TATB as a tan solid. A sample of this $Ac_3$-TATB (0.069 g, 0.18 mmol) is dissolved in 4 ml of ammonium hydroxide (28% $NH_3$ in water) to give a dark brown solution which is heated in a sealed pressure tube for 1 hr at 123° C. The resulting product is collected, washed ($NH_4OH$, water) and dried to yield 0.029 g TATB (62%) as dark tan solid containing DATB and TADNB (FTIR).

Example 12

Purification of $Ac_3$-TATB with Carbon and Conversion Back to TATB

Impure TATB was synthesized as follows: TATB (5.20 g, 20.0 mmol) containing 4% DATB (FTIR analysis) is suspended in 150 ml DMSO. Addition of 50% aqueous sodium hydroxide (1.60 ml, 30.6 mmol) and 50% aqueous hydroxylamine (2.00 ml, 32.6 mmol) and heating for 15 min at 90°

C. produces a deep burgundy solution. Reaction with carbon dioxide gas (introduced above the surface of the solution) for 30 min at 90° C. produces a dark suspension that is cooled to ambient temperature and filtered. The collected product is washed (DMSO, hot water) and dried to yield TATB as a dark olive drab material containing 4% DATB and 11% TADNB (FTIR).

The TATB containing 4% DATB and 11% TADNB is reacted with acetic anhydride and $H_2SO_4$ to provide $Ac_3$-TATB as a tan solid. A sample of the this $Ac_3$-TATB (0.069 g, 0.18 mmol) is dissolved in 2 ml of ammonium hydroxide and applied to a column of activated carbon ( 0.32 g Norit A®). Elution with ammonium hydroxide provides a clear, yellow solution of purified $Ac_3$-TATB in ammonium hydroxide which is heated for 1 hr (123° C.) to provide 0.027 g TATB (58%) as a light yellow solid with no detectable DATB or TADNB (FTIR). DSC (heating rate: 10° C./min) of the purified TATB gives an exotherm peak of 382.29° C. compared with an exotherm peak of 377.26° C. for production grade TATB prepared by the Benziger procedure (U.S. Pat. No. 4,032,377).

Samples of purified Ac3-TATB ammonolyzed in $NH_4OH$-DMF (3:1, v/v) and $NH_4OH$-DMF (1:3, v/v) provide TATB samples with DSC exotherm peaks of 384.86.29° C. and 382.90° C. respectively.

Throughout this application, various publications, patents, and published patent applications were referred to. The disclosures of the publications, patents, and published patent specifications referenced in this application are hereby incorporated by reference into the present disclosure to more fully describe the state of the art to which this invention pertains.

All numbers expressing quantities of ingredients, constituents, reaction conditions, and so forth used in the specification and claims are to be understood as being modified in all instances by the term "about". Notwithstanding that the numerical ranges and parameters setting forth the broad scope of the subject matter presented herein are approximations, the numerical values set forth in the specific examples are reported as precisely as possible. Any numerical value, however, inherently contain certain errors necessarily resulting from the standard deviation found in their respective testing measurements.

While various materials, parameters, operational sequences, etc. have been described to exemplify and teach the principles of this invention, such are not intended to be limited. Modifications and changes may become apparent to those skilled in the art; and it is intended that the invention be limited only by the scope of the appended claims.

The invention claimed is:

1. A method comprising:
   suspending picric acid or ammonium picrate with an ammonium salt in a dipolar aprotic solvent;
   heating the suspension under a pressure ranging from 20 to 80 psi to form picramide;
   converting said picramide via VNS chemistry to crude TATB;
   acetylating said crude TATB to form triacetyl-TATB;
   treating said triacetyl-TATB with activated carbon; and
   ammonolyzing said carbon-treated triacetyl-TATB to form purified TATB.

2. The method recited in claim 1, wherein the mole equivalents of ammonium salt to picric acid ranges from 2 to 30 and the mole equivalents of ammonium salt to ammonium picrate ranges from 1 to 30.

3. The method recited in claim 1, wherein said ammonium salt is selected from the group consisting of diammonium hydrogen phosphate, ammonium carbamate, ammonium bicarbonate and ammonium acetate.

4. The method recited in claim 1, wherein the dipolar aprotic solvent is selected from the group consisting of sulfolane and N-methylpyrrolidinone.

5. The method recited in claim 1, wherein said heating is to a temperature in the range of 175 to 185° C.

6. The method recited in claim 1, wherein said acetylation is accomplished using acetic anhydride and sulfuric acid.

7. The method recited in claim 1, wherein said ammonolyzing is accomplished by using ammonium hydroxide and heat.

8. The method recited in claim 7, wherein said heat is at a temperature ranging from 90–130° C. for a period of time ranging from 0.5–4 hours.

9. A method comprising:
   suspending picric acid or ammonium picrate with an ammonium salt in a dipolar aprotic solvent; and
   heating the suspension to a temperature in the range of 175 to 185° C. under a pressure ranging from 20 to 80 psi to form picramide.

10. A method comprising:
    providing crude TATB with impurities ranging from 1–15%;
    acetylating said crude TATB to form triacetyl-TATB;
    treating said triacetyl-TATB with activated carbon; and
    ammonolyzing said carbon-treated triacetyl-TATB to form purified TATB.

* * * * *